United States Patent [19]

Kobayashi et al.

[11] Patent Number: 5,476,668
[45] Date of Patent: Dec. 19, 1995

[54] BASE FOR FILM-COATING PHARMACEUTICALS AND METHOD FOR PREPARING SAME

[75] Inventors: Kazuto Kobayashi; Junichi Watanabe; Shinichiro Nakamura, all of Nakakubiki, Japan

[73] Assignee: Shin-Etsu Chemical Co., Ltd., Japan

[21] Appl. No.: 168,411

[22] Filed: Dec. 17, 1993

Related U.S. Application Data

[62] Division of Ser. No. 773,910, filed as PCT/JP91/01126, Aug. 1991, abandoned.

[30] Foreign Application Priority Data

Aug. 24, 1990 [JP] Japan ................... 2-223728

[51] Int. Cl.$^6$ .................... C08B 11/00; C08B 11/12
[52] U.S. Cl. ................ 424/494; 424/488; 424/490; 536/98
[58] Field of Search ................... 424/468, 469, 424/470, 488, 494, 490; 536/88, 84, 85, 86, 87, 98

[56] References Cited

U.S. PATENT DOCUMENTS

| | | | |
|---|---|---|---|
| 2,118,663 | 5/1938 | Bradshaw | 536/89 |
| 2,118,664 | 5/1938 | Bradshaw | 536/89 |
| 2,178,630 | 11/1939 | Finlayson | 536/89 |
| 3,391,135 | 7/1968 | Ouno et al. | 536/58 |
| 3,549,617 | 12/1970 | Whitmeyer | 536/89 |
| 3,728,331 | 4/1973 | Savage | 536/88 |
| 4,063,018 | 12/1977 | Ohnaka et al. | 536/98 |
| 4,091,205 | 5/1978 | Onda et al. | 536/85 |
| 4,250,305 | 2/1981 | Saito et al. | 536/84 |
| 4,259,314 | 3/1981 | Lowey | 424/469 |
| 4,366,310 | 12/1982 | Leslie | 424/488 |
| 4,369,172 | 1/1983 | Schor et al. | 424/468 |
| 4,678,516 | 7/1987 | Alderman et al. | 424/488 X |
| 4,695,591 | 9/1987 | Hanna et al. | 424/488 X |
| 5,008,113 | 4/1991 | Kokubo et al. | 424/480 |

FOREIGN PATENT DOCUMENTS

| | | |
|---|---|---|
| 0210917 | 2/1987 | European Pat. Off. . |
| 0276813 | 8/1988 | European Pat. Off. . |
| 3009149 | 9/1981 | Germany . |

Primary Examiner—Melvyn I. Marquis
Assistant Examiner—Robert H. Harrison
Attorney, Agent, or Firm—Parkhurst, Wendel & Rossi

[57] ABSTRACT

A cellulose ether having a low degree of polymerization is used as a base for film-coating pharmaceuticals. The cellulose ether having a low degree of polymerization obtained by causticizing a pulp having a copper number of not more than 0.4 g, adding an etherifying agent to form a cellulose ether having a high degree of polymerization, then refining it with hot water, drying by heating, finely pulverizing the dried cellulose ether and depolymerizing the fine powder has high whiteness and is thus suitable for use as a base for film-coating pharmaceuticals. The viscosity of a 2% aqueous solution of the cellulose having a low degree of polymerization is preferably not more than 20 cSt at 20° C. The cellulose having a low degree of polymerization is selected from methyl cellulose, hydroxymethyl cellulose, hydroxyethyl cellulose, hydroxypropyl cellulose, hydroxypropyl methyl cellulose and hydroxybutyl methyl cellulose. The cellulose ether having a high degree of polymerization is pulverized within one minute in an impact pulverizer after drying it at a temperature of atmosphere of not more than 100° C. and that of the cellulose ether per se of 40° to 80° C. to control the moisture content thereof to 1 to 5% by weight, and thus a cellulose ether having a low degree of polymerization and high whiteness can be obtained.

4 Claims, 1 Drawing Sheet

BASE FOR FILM-COATING PHARMACEUTICALS AND METHOD FOR PREPARING SAME

This is a Division of application Ser. No. 07/773,910 filed as PCT/JP91/01126, Aug. 26, 1991, now abandoned.

TECHNICAL FIELD

The present invention relates to a cellulose ether having high whiteness and a low degree of polymerization used as a base for film-coating pharmaceuticals as well as a method for preparing the same.

BACKGROUND ART

The film-coating applied to pharmaceutical preparations makes it possible to mask the bitter taste of the pharmaceuticals, to increase the hardness of the resulting pharmaceuticals and to impart a smooth surface to them. As bases for use in the film-coating treatment, there 20 have in general been employed, for instance, water-soluble cellulose ethers having a low degree of polymerization. The term "cellulose ethers having a low degree of polymerization" means cellulose ethers whose 2% aqueous solution has a viscosity of not more than 20 cSt (centistokes) as determined at 20° C. and can be obtained by depolymerization of cellulose ethers having a high degree of polymerization.

The cellulose ethers having a high degree of polymerization can be prepared by converting purified pulp into an alkaline cellulose and then reacting the alkaline cellulose with an etherifying agent. After the etherification, the cellulose ether having a high degree of polymerization is refined with hot water, dried and then finely pulverized to an average particle size of the order of 50 μm. The fine powder thus obtained is depolymerized. As depolymerization methods, there have been known, for instance, a method in which hydrogen chloride gas is used (Japanese Patent Publication No. 48-41037) and a method which comprises acting hydrogen peroxide on such fine powder (Japanese Patent Publication No. 45-678).

However, the cellulose ethers having a low degree of polymerization prepared by the foregoing methods have a tinge of gray or yellowish color and accordingly, if pharmaceuticals are film-coated with the cellulose ethers as bases, the pharmaceuticals seem to be colored due to the influence of the bases. For this reason, pharmaceuticals have currently been pigmented to impart good appearance to them by incorporating a coloring agent into the base upon film-coating the same. In this case, however, the color tone of the resulting pharmaceuticals is not clear due to the color of the base per se and the commercial value thereof is impaired. Therefore, the cellulose ethers having a low degree of polymerization as bases must have high whiteness.

To further improve the whiteness of the cellulose ethers, there have been proposed methods which comprise acting bisulfite ions (Japanese Patent Publication No. 46-41628) or sulfur dioxide (Japanese Patent Provisional Publication No. 52-152985) on the cellulose ethers in a water-soluble fatty acid alcohol to bleach or decolorize the same. However, these methods comprise complicated processes and sulfur-containing compounds remain in the resulting product as impurities. It has also been tried to improve the whiteness of the base by limiting the amount of water during reaction (Japanese Patent Provisional Publication No. 62-25101). However, this method cannot provide whiteness higher than a certain level.

The inventors of this invention have investigated the reason why the cellulose ethers having a low degree of polymerization are colored yellow or brown and taken note of the phenomenon that when the cellulose ethers having a high degree of polymerization are hydrolyzed with an acid, the yellow index of the cellulose ethers is increased simultaneously with a decrease in the viscosity thereof. The cellulose ether is dissolved in water to give a 2% aqueous solution thereof, the yellow index thereof is determined by SM Color Computer "SM-4" available from Suga Testing Machine Manufacturing Co., Ltd. and is used as the index for the whiteness.

FIG. 1 shows the relation between the wavelength of ultraviolet rays (NM) and the absorbance (A) of 2% aqueous solutions of cellulose ethers having different viscosities (3 cSt, 6 cSt and 500 cSt), the cellulose ether used being hydroxypropyl methyl cellulose. In FIG. 1, the absorbance shows two peaks in the vicinity of the UV wavelength of 230 and 280 nm. The lower the viscosity, i.e., the lower the degree of polymerization, the higher the absorbance at the peaks and, therefore, it can be assumed that a substance which has such peaks and becomes a cause of such a high yellow index is formed or present in a large amount in the cellulose ether having a low degree of polymerization.

The substance can be extracted from the hydroxypropyl methyl cellulose aqueous solution with diethyl ether. Moreover, it can be confirmed that the hydroxypropyl methyl cellulose aqueous solution from which the substance is removed by extraction has a reduced yellow index. However, the correct structure of the substance exhibiting such peaks has not yet been established. The substance is probably a product having chromophoric groups such as carbonyl and/or carboxyl groups formed through the oxidation of hydroxyl groups of the cellulose. It is also assumed that the glucose having groups formed through the modification of the cellulose due to oxidation is decomposed to give the substance capable of being extracted with the ether. The yellow index of an aqueous solution of the hydroxypropyl methyl cellulose from which this substance is extracted with ether is reduced, but it is still higher than that of the cellulose prior to the hydrolysis. This indicates that other chromophoric substances which cannot be extracted with ether would still remain in the aqueous solution of the hydroxypropyl methyl cellulose. Thus, there is a limit in the improvement of the whiteness by ether extraction. Furthermore, another extraction process is required for the preparation of cellulose ethers having a low degree of polymerization. The use of the ether extraction of the chromophoric substance in addition to the foregoing extraction process makes the production process complicated and thus is not proper.

DISCLOSURE OF THE INVENTION

An object of the present invention is to provide a cellulose ether having a high whiteness and a low degree of polymerization which can be used as a base for film-coating pharmaceuticals.

The base for film-coating pharmaceuticals for achieving the foregoing object is a cellulose ether having a low degree of polymerization which is prepared by causticizing a pulp having a copper number of not more than 0.4 g, adding an etherifying agent to form a cellulose ether having a high degree of polymerization, then refining it with hot water, drying by heating, finely pulverizing the dried cellulose ether and depolymerizing the fine powder.

Another object of the present invention is to provide a method for preparing a cellulose ether having a high whiteness and a low degree of polymerization which can be used as a base for film-coating pharmaceuticals.

The method for preparing a base for film-coating pharmaceuticals for achieving the second object comprises the steps of causticizing a pulp having a copper number of not more than 0.4 g, adding an etherifying agent to form a cellulose ether having a high degree of polymerization, then refining it with hot water, drying by heating, finely pulverizing the dried cellulose ether and depolymerizing the fine powder.

BEST MODE FOR CARRYING OUT THE INVENTION

The inventors of this invention have investigated the relation between the modification through oxidation and the yellow index of a cellulose ether having a low degree of polymerization and have completed the foregoing inventions. The higher the degree of modification through oxidation of the cellulose ether having a low degree of polymerization, the greater the extent of pigmentation thereof.

Under such circumstances, the inventors of this invention have first investigated the copper number of starting pulps as a measure for the modification of cellulose ethers through oxidation. The copper number indicates the amount of the reducing carbonyl groups present in the pulp. In other words, the greater the amount of the carbonyl groups or the higher the copper number, the higher the degree of modification of the pulp through oxidation. A pulp having a high copper number was used and it was investigated whether the resulting cellulose ether had a high yellow index or not. To this end, hydroxypropyl methyl celluloses were prepared from pulps having a variety of copper numbers and the UV absorbance of each sample was determined. In this connection, the copper number of the pulps were determined according to JIS P8101 "Test Method for Dissolved Pulp" and TAPPI T430.

The following Table 1 shows the copper numbers of three kinds of pulps A, B and C, and the results of UV absorbance determination performed at a wavelength of 200 nm using 2% aqueous solutions (viscosity 500 cSt) of hydroxypropyl methyl celluloses obtained from the pulps A, B and C.

TABLE 1

| Pulp | A | B | C |
|---|---|---|---|
| Copper Number (g) | 0.65 | 0.34 | 0.21 |
| Absorbance of HPMC at 200 nm | 0.84 | 0.78 | 0.65 |

HPMC: hydroxypropyl methyl cellulose

The pulps A and B were prepared from Southern Pine as a starting material while the pulp C was obtained from cotton linter as a starting material. The pulps A and B were prepared according to the kraft process.

Figure 1:
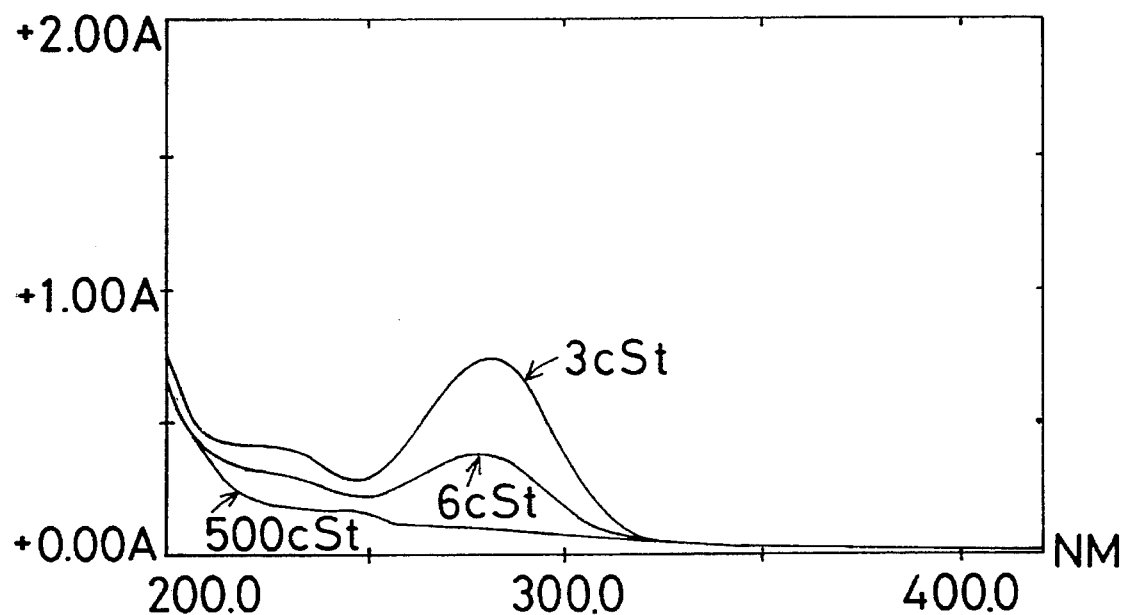
FIG. 1 is a graph showing the relation between the viscosity and UV absorbance of a 2% aqueous solution of hydroxypropyl methyl cellulose.
Figure 2:
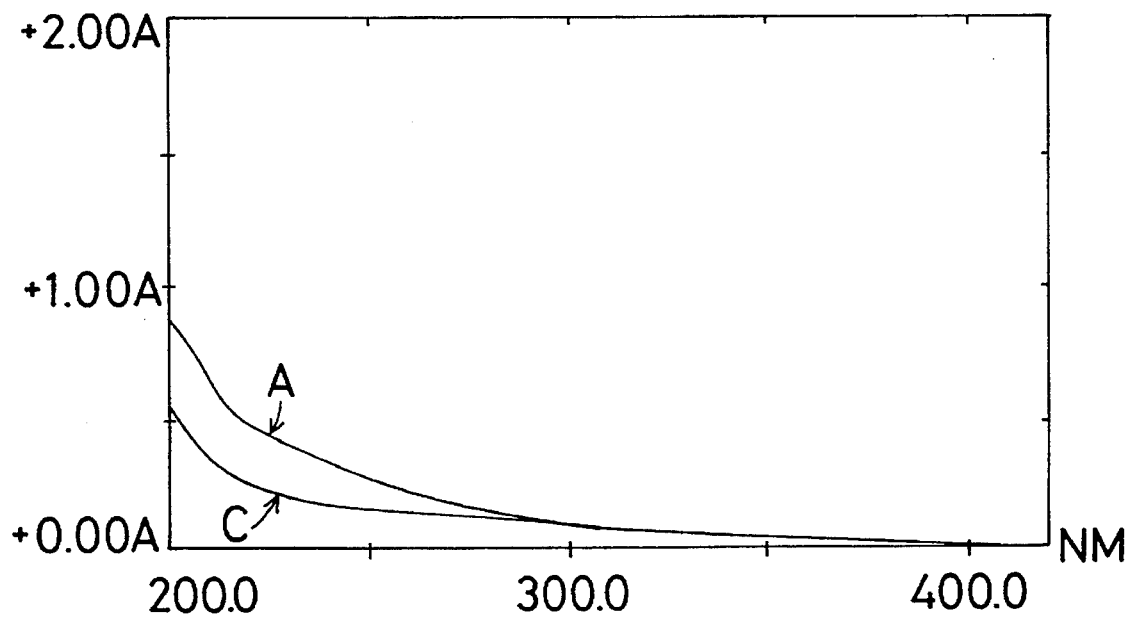
FIG. 2 is a graph showing the relation between the wavelength of UV light and the absorbance of 2% aqueous solutions (viscosity 500 cSt) of hydroxypropyl methyl celluloses obtained from different kinds of pulps.

FIG. 2 is a graph showing the relation between the wavelength (NM) of UV light and absorbance (A) of 2% aqueous solutions (viscosity 500 cSt) of hydroxypropyl methyl celluloses obtained from different kinds of pulps.

As a result, the copper number of pulp correlates to the UV absorbance of an aqueous solution of cellulose ether prepared, at a wavelength of 200 nm. It is assumed that the UV absorbance at 200 nm is due to the presence of carboxyl groups included in the cellulose ether. These results indicate that a cellulose ether having a low degree of polymerization which has a large number of carbonyl groups or a high yellow index is obtained from a pulp having a high copper number. Paradoxically speaking, if a pulp having a low copper number is selected as a starting material, a cellulose ether having a low degree of polymerization and a low yellow index would be obtained.

Thus, the cellulose ether having a low degree of polymerization used for preparing the base for film-coating pharmaceuticals is preferably prepared from a pulp having a low copper number as a starting material to form a cellulose ether having high whiteness. More specifically, it is preferred to use a pulp having a copper number of not more than 0.4 g as a starting material. This is because, if the copper number of the starting pulp is greater than 0.4 g, the resulting cellulose ether having a low degree of polymerization is extremely colored and insufficient for use as a base for film-coating pharmaceuticals.

The cellulose ether having a high degree of polymerization is prepared by mixing wood/cotton pulp (cellulose) as a starting material with an aqueous solution of an alkali metal hydroxide, etherifying with an alkyl halide and/or an alkylene oxide, then washing with, for instance, hot water and drying by heating.

Moreover, the inventors of this invention have taken note of the process for drying a cellulose ether having a high degree of polymerization by heating as a measure of the modification thereof through oxidation. As a result, the inventors have found out that the process for drying by heating closely relates to the yellow index of the resulting cellulose ether having a low degree of polymerization.

It is necessary to adjust the moisture content of the cellulose ether having a high degree of polymerization to 1 to 5% by weight after drying the same. If the moisture content thereof is less than 1% by weight, the whiteness of the resulting cellulose ether having a low degree of polymerization is impaired, while if it exceeds 5% by weight, the rate of the subsequent depolymerization process is low, the productivity of the cellulose ether having a low degree of polymerization is correspondingly low and thus the use of such a cellulose ether is not practicable. Further, the drying process must be performed so that the moisture content of the cellulose ether is not reduced to less than 1% by weight. More specifically, if the moisture content of the cellulose ether having a high degree of polymerization is once reduced to less than 1% by weight and then the moisture content is adjusted to 1 to 5% by weight, the whiteness of the cellulose ether having a low degree of polymerization obtained by depolymerization of the cellulose ether having a high degree of polymerization is never improved.

In the drying process, the temperature of the substance to be dried (the temperature of the cellulose ether having a high degree of polymerization) is preferably maintained in the range of from 40 to 80° C. If it is less than 40° C., it takes a long period of time for drying and thus the productivity is lowered. On the other hand, if it exceeds 80° C., the whiteness of the cellulose ether obtained after the depolymerization is impaired. In addition, it is preferred to maintain the temperature of walls of jacket and tubes of the dryer which come in contact with the cellulose ether and the gas circulated within the dryer for drying the cellulose ether to not more than 100° C. If the temperature is more than 100° C., the whiteness of the final product may be lowered because of local heating thereof even if the temperature of the product is maintained at a temperature of not more than 80° C.

The drying may be performed in air, but preferably in an inert gas atmosphere such as nitrogen gas or under reduced pressure substantially free of oxygen gas.

In the foregoing drying process, there may be used dryers currently used such as a tray dryer, a fluid dryer, an agitation type dryer and a tube type dryer.

After the completion of the drying, the resulting cellulose ether having a high degree of polymerization is pulverized into pieces having a predetermined size.

Furthermore, the inventors of this invention have taken note of the time required for the pulverization process as a measure for the modification of the cellulose ether through oxidation. If the cellulose ether having a high degree of polymerization is finely pulverized to an average particle size in the order of 50 μm, the resulting powder has good handling properties, an improved solubility and good handling properties (fluidability of the powder) during the subsequent hydrolysis. However, if the pulverization time is too long, the cellulose ether having a high degree of polymerization is liable to be modified through oxidation. Incidentally, a ball mill has currently been used as a pulverization machine.

The inventors have investigated the correlation between the time required for the pulverization of hydroxypropyl methyl cellulose into powder having a particle size of the order of 50 μm with a ball mill and the UV absorbance of the pulverized hydroxypropyl methyl cellulose or the yellow index of the cellulose ether having a low degree of polymerization obtained after depolymerizing the pulverized hydroxypropyl methyl cellulose. As a result, it has been confirmed that the UV absorbance at 200 nm which corresponds to the carbonyl and/or carboxyl groups resulting from the modification of the glucose hydroxyl groups through oxidation is increased and the yellow index of the resulting cellulose ether having a low degree of polymerization is likewise increased as the pulverization time increases. Accordingly, the modification of the cellulose ether through oxidation can be eliminated by shortening pulverization time required.

A suitable pulverizer which makes it possible to pulverize within a short period of time is an impact pulverizer and preferably those capable of pulverizing the cellulose ether to a particle size of the order of 50 μm within one minute. An impact pulverizer comprises a combination of a blade rotating at a high speed and an impact plate arranged along with the blade, or an impact plate rotating at a high speed and a blade disposed within the pulverizing chamber. The ingredient fed to the pulverizing chamber is pulverized through collision between the ingredient to be pulverized and the impact plate or between ingredients moving at a high speed.

Specific examples of the impact pulverizers are Turbo mill (available from Turbo Industries, Ltd.), PPSR (available from Balmann co., Ltd.), ACM (available from Hosokawa Micron Co., Ltd.) and Victory Mill (available from Hosokawa Micron Co., Ltd.). In addition to the foregoing examples, Jet Mill (available from Nippon Pneuma Co., Ltd.) may also be used, in which the ingredient is pulverized by colliding it together with a highly compressed gas with a fixed impact plate. These impact pulverizers permit the pulverization within one minute and some of these can complete the pulverization within several seconds.

The cellulose ether having a high degree of polymerization which is pulverized into powder having an average particle size of the order of 50 μm provides a cellulose ether having a low degree of polymerization and an improved whiteness by depolymerizing the same in accordance with the known method.

The yellow index of the cellulose ether having a low degree of polymerization obtained by depolymerizing the cellulose ether which has been finely pulverized with these impact pulverizer is identical with that observed for the cellulose ether having a low degree of polymerization obtained by depolymerizing the cellulose ether which is not pulverized.

In the present invention, the cellulose ether having a high degree of polymerization obtained by causticizing a starting pulp and then treating the causticized pulp with an etherifying agent (2% aqueous solution) has a viscosity, as determined at 20° C., of not less than 20 cSt, preferably several tens to several hundreds cSt. Examples thereof include alkyl and hydroxyalkyl celluloses such as methyl cellulose, hydroxymethyl cellulose and hydroxyethyl cellulose; and hydroxyalkyl alkyl celluloses such as hydroxypropyl methyl cellulose and hydroxybutyl methyl cellulose.

The iscosity of the cellulose ether having a low degree of polymerization (as a 2% aqueous solution) obtained by depolymerization of a cellulose ether having a high degree of polymerization, as determined at 20° C. is preferably not more than 20 cSt and examples of such cellulose ethers having a low degree of polymerization include, corresponding to the starting cellulose ethers having a high degree of polymerization, alkyl and hydroxyalkyl celluloses such as methyl cellulose, hydroxymethyl cellulose and hydroxyethyl cellulose; and hydroxyalkyl alkyl celluloses such as hydroxypropyl methyl cellulose and hydroxybutyl methyl cellulose.

The specific embodiments of the present invention will hereinafter be explained with reference to the following Examples, but the present invention is by no means limited to these Examples.

EXAMPLE 1

Wood pulp (300 g) was impregnated with 730 g of a 49% aqueous solution of sodium hydroxide and then charged in a 5 l autoclave. To the autoclave, there were added 474 g of methyl chloride and 160 g of propylene oxide and the mixture was reacted at 50° to 85° C. for 4 hours. The resulting hydroxypropyl methyl cellulose was washed with 20 l of hot water and then dehydrated to adjust the water content to 50% by weight. This was introduced into an agitation type dryer and dried for 2 hours while controlling the temperature of the walls of the dryer and the air for drying to 90° C. The maximum temperature of the substance to be dried was 70° C. during the drying process. The moisture content of the substance after drying was 2.0% by weight. The product was pulverized by an impact pulverizer to give a hydroxypropyl methyl cellulose having a high degree of polymerization whose 2% aqueous solution had a viscosity of 400 cSt at 20° C.

To the hydroxypropyl methyl cellulose having a high degree of polymerization, there was added a 0.5% by weight hydrogen chloride, in the form of an aqueous solution, so that the total amount of the moisture was equal to 5% by weight on the basis of the hydroxypropyl methyl cellulose and the mixture was admixed by stirring. The mixture was subjected to depolymerization for 2 hours while maintaining the temperature of the mixture at 70° C. to thus give a hydroxypropyl methyl cellulose having a low degree of polymerization whose 2% aqueous solution had a viscosity of 6 cSt at 20° C.

The yellow index of the 2% aqueous solution of the cellulose was determined by SM color Computer "SM-4" (available from Suga Testing Machine Manufacturing Co., Ltd.) and was found to be YI=10. This value of YI was used as the index for whiteness.

Comparative Example 1

After preparing a hydroxypropyl methyl cellulose having a moisture content of 50% by weight in the same manner used in Example 1, the cellulose was dried at a dryer wall-temperature of 120° C. and a hot air-temperature of 90° C. for 1.5 hour in the air. The maximum temperature of the cellulose was 85° C. and the final moisture content thereof was 0.5% by weight during the drying process. The resulting hydroxypropyl methyl cellulose was depolymerized in the same manner used in Example 1. Thus, a hydroxypropyl methyl cellulose having a low degree of polymerization was obtained and the viscosity of a 2% aqueous solution thereof as determined at 20° C. was 6 cSt. The yellow index thereof was determined in the same manner used in Example 1 and was found to be YI=13.

EXAMPLE 2

After preparing a hydroxypropyl methyl cellulose having a moisture content of 50% by weight in the same manner used in Example 1, the cellulose was dried for one hour in a dryer in which the wall-temperature was 120° C. and a hot air-temperature was 90° C. The maximum temperature of the cellulose was 70° C. and the final moisture content thereof was 2.0% by weight during the drying process. The resulting hydroxypropyl methyl cellulose was depolymerized in the same manner used in Example 1. Thus, a hydroxypropyl methyl cellulose having a low degree of polymerization was obtained and the viscosity of a 2% aqueous solution thereof as determined at 20° C. was 6 cSt. The yellow index thereof was determined in the same manner used in Example 1 and was found to be YI=11.

EXAMPLE 3

After preparing a hydroxypropyl methyl cellulose having a moisture content of 50% by weight in the same manner used in Example 1, the cellulose was dried for 2 hours in a dryer in which the wall-temperature was 90° C. and a nitrogen gas temperature in the dryer was 90° C. The maximum temperature of the cellulose was 70° C. and the final moisture content thereof was 2.0% by weight during the drying process. The resulting hydroxypropyl methyl cellulose was depolymerized in the same manner used in Example 1. Thus, a hydroxypropyl methyl cellulose having a low degree of polymerization was obtained and the viscosity of a 2% aqueous solution thereof as determined at 20° C. was found to be 6 cSt. The yellow index thereof was determined in the same manner used in Example 1 and was found to be YI=9.

EXAMPLES 4 and 5 and Comparative Examples 2 to 4

In Examples 4 and 5 and Comparative Examples 2 to 4, hydroxypropyl methyl celluloses (methoxy content, 29%; hydroxypropyl content, 9%) were prepared using pulps each having a copper number as listed in Table 2 according to the following manner. First, a refined pulp was impregnated in a 50% by weight aqueous solution of sodium hydroxide to prepare an alkali cellulose having 34% by weight sodium hydroxide. To the alkali cellulose, there were added methyl chloride in a molar amount equal to that of sodium hydroxide and propylene oxide in an amount of 1.5 time the molar amount of cellulose and the mixture was introduced into a pressure vessel. The etherifying reaction was continued at 50° to 90° C. for 4 hours and after the completion of the reaction, the reaction system was purified with hot water. Thereafter, each product was dried under the drying conditions as defined in Table 2. After drying, hydroxypropyl methyl celluloses each having a moisture content as listed in Table 2 were obtained.

Each resulting hydroxypropyl methyl cellulose was finely pulverized in a pulverizer as listed in Table 2 to an average particle size of the order of 50 μm. The pulverization time for each case was specified in Table 2. The viscosity of the finely pulverized hydroxypropyl methyl cellulose (a 2% aqueous solution) as determined at 20° C. was 500 cSt. The depolymerization was carried out by adding, to this hydroxypropyl methyl cellulose having a high degree of polymerization, 12% hydrochloric acid in an amount of 0.0030 part by weight with respect to the amount of the hydroxypropyl methyl cellulose. The viscosity of a 2% aqueous solution of the cellulose after the depolymerization was 6 cSt. The yellow index of each hydroxypropyl methyl cellulose having a low degree of polymerization was determined.

Then a 6% aqueous solution was prepared from each sample of the hydroxypropyl methyl celluloses. White tablets which mainly comprised milk sugar and corn starch and had a diameter of 8 mm and a weight of 200 m g/tablet were coated with the aqueous solution in a coated amount of 8 m g/tablet. The total weight of the tablets coated was 1.5 k g. The coating operation was carried out using Pan Coating Apparatus FM-2 (available from Freunt Sangyo K.K.). The yellow indexes of the coated tablets were determined by the foregoing SM Color Computer. The results thus obtained are summarized in Table 2. The yellow index was also determined after allowing the tablets to stand at 40° C. and a relative humidity (RH) of 75% for one month. The results thus obtained are also listed in Table 2.

TABLE 2

| Example No. | 4 | 5 | 2* | 3* | 4* |
|---|---|---|---|---|---|
| Copper Number of Pulp (g) | 0.34 | 0.21 | 0.65 | 0.21 | 0.21 |
| Drying Process: | | | | | |
| Temp. of Substance (°C.) | 70 | 70 | 70 | 90 | 70 |
| Wall Temp (°C.) | 90 | 90 | 90 | 120 | 90 |
| Atmosphere | $N_2$ gas | $N_2$ gas | $N_2$ gas | air | $N_2$ gas |
| Moisture After Drying (wt %) | 2.0 | 2.0 | 2.0 | 0.3 | 2.0 |
| Pulverization Process: | | | | | |
| Pulverizer | ACM | ACM | ACM | ACM | ball mill |
| Pulverization time (min) | 0.1 | 0.1 | 0.1 | 0.1 | 120 |

TABLE 2-continued

| Example No. | 4 | 5 | 2* | 3* | 4* |
|---|---|---|---|---|---|
| Yellow Index (YI) of LDP-HPMC | 8.0 | 7.0 | 11.0 | 9.0 | 13.0 |
| YI of Tablet Coated with LDP-HPMC | 4.1 | 3.3 | 6.3 | 5.2 | 7.9 |
| YI of Tablet After Allowing to Stand | 5.6 | 4.3 | 8.7 | 7.2 | 11.0 |

*Comparative Example
LDP-HPMC: hydroxypropyl methyl cellulose having a low degree of polymerization Industrial Applicability The cellulose ether having a low degree of polymerization provided by the present invention has whiteness extremely higher than that for the cellulose ethers prepared by the conventional techniques. Moreover, the used of the cellulose ether as a base for film-coating pharmaceuticals makes it possible to provide pharmaceuticals excellent in whiteness and having a clear color even if they are pigmented. Furthermore, the method of the present invention does not require a bleaching process and makes it possible to easily provide cellulose ethers which have a low degree of polymerization and high whiteness and are free of impurities at a low cost.

We claim:

1. A method for preparing a base for film-coating pharmaceuticals comprising a cellulose ether having a low degree of polymerization characterized by a viscosity of no more than 20 cSt at 20° C. when said cellulose ether is in the form of a 2% aqueous solution, said method comprising (a) causticizing a cellulose pulp having a copper number of not more than 0.4 g;

(b) adding an alkyl etherifying agent to the causticized pulp of step (a) to form a cellulose ether having a high degree of polymerization;

(c) refining the cellulose ether of step (b) with water;

(d) drying the cellulose ether of step (c) by heating at a temperature not to exceed 80° C. and such that the moisture content of the cellulosic ether at no time falls to less than 1% by weight;

(e) finely pulverizing the dried cellulose ether of step (d) in an impact pulverizer for no more than a minute while maintaining the moisture content of the cellulose ether having a high degree of polymerization in the range of 1 to 5% by weight; and (f) depolymerizing the finely pulverized dried cellulose ether of step (e) to form a base for film-coating pharmaceuticals comprising a cellulose ether having said low degree of polymerization.

2. The method of claim 1 wherein the atmosphere of drying step (d) is maintained at a temperature of no more than 100° C. and the temperature of the cellulose ether having a high degree of polymerization is maintained at 40° to 80° C.

3. The method of claim 1 wherein step (d) is carried out in an inert gas or in an oxygen-free atmosphere.

4. The method of claim 1 wherein the cellulose ether having a low degree of polymerization is selected from the group consisting of methyl cellulose, hydroxymethyl cellulose, hydroxyethyl cellulose, hydroxyopropyl cellulose, hydroxyethyl methyl cellulose, hydroxypropyl methyl cellulose, and hydroxylbutyl methyl cellulose.

* * * * *